(12) United States Patent
Burgherr et al.

(10) Patent No.: US 10,349,981 B2
(45) Date of Patent: Jul. 16, 2019

(54) METHODS AND SYSTEMS FOR ADJUSTING AN EXTERNAL FIXATION FRAME

(71) Applicant: Stryker European Holdings I, LLC, Kalamazoo, MI (US)

(72) Inventors: Vinzenz Andreas Burgherr, Bern (CH); Adam John Edelhauser, Nyack, NY (US); Yves Stephane Crozet, Ramsey, NJ (US); Marcel Aeschlimann, Ligerz (CH); Christoph Dworzak, Oberthal (CH); Antonino Lanci, Bern (CH); Markus Mast, Bern (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 49 days.

(21) Appl. No.: 15/621,495

(22) Filed: Jun. 13, 2017

(65) Prior Publication Data
US 2017/0277859 A1 Sep. 28, 2017

Related U.S. Application Data

(60) Continuation of application No. 14/263,240, filed on Apr. 28, 2014, which is a division of application No. 13/167,101, filed on Jun. 23, 2011.

(51) Int. Cl.
*A61B 17/66* (2006.01)
*A61B 17/62* (2006.01)
(Continued)

(52) U.S. Cl.
CPC .............. *A61B 17/66* (2013.01); *A61B 17/62* (2013.01); *A61B 34/10* (2016.02); *A61B 90/98* (2016.02);
(Continued)

(58) Field of Classification Search
CPC ......... G06F 19/00; A61B 34/10; A61B 90/98; A61B 17/62; A61B 17/66;
(Continued)

(56) References Cited

U.S. PATENT DOCUMENTS

| 4,365,624 A | 12/1982 | Jaquet |
| 4,570,625 A | 2/1986 | Harris et al. |

(Continued)

FOREIGN PATENT DOCUMENTS

| EP | 0386912 A1 | 9/1990 |
| FR | 2576774 A1 | 8/1986 |

(Continued)

OTHER PUBLICATIONS

"Basic Ilizarov Techniques," Techniques in Orthopaedics®, vol. 5, No. 4, Dec. 1990, pp. 55-59.
(Continued)

*Primary Examiner* — Ellen C Hammond
*Assistant Examiner* — Tessa M Matthews
(74) *Attorney, Agent, or Firm* — Lerner, David, Littenberg, Krumholz & Mentlik, LLP

(57) ABSTRACT

A tool for implementing a correction plan in an external fixation frame having a plurality of adjustment elements or screws, for example, generally includes a driver, a motor, a controller, and a processor. The driver is adapted to engage and rotate each of the screws. The motor is coupled the driver and adapted to rotate the driver. The controller is connected to the motor and configured to control operation of the motor. The a processor adapted configured to: receive correction plan data; receive identification data including information for identifying at least one of the plurality of screws; determine movement of at least one of the plurality of the screws based on the correction plan data and the identification data; and send signals indicative of the deter-
(Continued)

mined movement to the controller in order to rotate at least one of the plurality of screws according to a predetermined correction plan.

13 Claims, 11 Drawing Sheets

(51) Int. Cl.
  *A61B 90/98* (2016.01)
  *A61B 34/10* (2016.01)
  *G16H 50/50* (2018.01)
  *A61B 90/00* (2016.01)

(52) U.S. Cl.
  CPC ........ *G16H 50/50* (2018.01); *A61B 2034/104* (2016.02); *A61B 2090/061* (2016.02); *A61B 2090/067* (2016.02); *F04C 2270/0421* (2013.01)

(58) Field of Classification Search
  CPC ........ A61B 2034/104; A61B 2090/061; A61B 2090/067; G16H 50/50; F04C 2270/0421
  See application file for complete search history.

(56) References Cited

U.S. PATENT DOCUMENTS

| | | | |
|---|---|---|---|
| 4,615,338 A | 10/1986 | Ilizarov et al. | |
| 4,973,331 A | 11/1990 | Pursley et al. | |
| 4,978,348 A | 12/1990 | Ilizarov | |
| 5,014,794 A | 5/1991 | Hansson | |
| 5,108,394 A | 4/1992 | Kurokawa et al. | |
| 5,156,605 A | 10/1992 | Pursley et al. | |
| 5,180,380 A | 1/1993 | Pursley et al. | |
| 5,334,202 A | 8/1994 | Carter | |
| 5,681,309 A | 10/1997 | Ross, Jr. et al. | |
| 5,702,389 A | 12/1997 | Taylor et al. | |
| 5,728,095 A | 3/1998 | Taylor et al. | |
| 5,971,984 A | 10/1999 | Taylor et al. | |
| 6,030,386 A * | 2/2000 | Taylor .................... | A61B 17/62 606/54 |
| 6,701,174 B1 * | 3/2004 | Krause ................. | A61B 17/025 600/407 |
| 7,955,334 B2 | 6/2011 | Steiner et al. | |
| 8,157,800 B2 | 4/2012 | Vvedensky et al. | |
| 8,257,353 B2 | 9/2012 | Wong et al. | |
| 8,282,652 B2 | 10/2012 | Mackenzi et al. | |
| 8,382,756 B2 | 2/2013 | Pool et al. | |
| 8,551,092 B2 | 10/2013 | Morgan et al. | |
| 8,702,705 B2 | 4/2014 | Ziran et al. | |
| 2002/0010465 A1 * | 1/2002 | Koo ........................ | A61B 17/62 606/57 |
| 2003/0191466 A1 | 10/2003 | Austin et al. | |
| 2004/0068187 A1 | 4/2004 | Krause et al. | |
| 2004/0073211 A1 * | 4/2004 | Austin .................... | A61B 17/62 606/54 |
| 2005/0215997 A1 | 9/2005 | Austin et al. | |
| 2005/0234448 A1 | 10/2005 | McCarthy | |
| 2006/0195198 A1 | 8/2006 | James | |
| 2007/0055234 A1 | 3/2007 | McGrath et al. | |
| 2007/0219561 A1 | 9/2007 | Lavallee et al. | |
| 2008/0051779 A1 | 2/2008 | Mackenzie et al. | |
| 2008/0178713 A1 * | 7/2008 | Long ..................... | B23P 19/066 81/467 |
| 2008/0228185 A1 | 9/2008 | Vasta et al. | |
| 2008/0269741 A1 | 10/2008 | Karidis | |
| 2008/0281332 A1 * | 11/2008 | Taylor ................ | A61B 17/1626 606/104 |
| 2010/0087819 A1 | 4/2010 | Mullaney | |
| 2010/0152604 A1 | 6/2010 | Kaula et al. | |
| 2011/0004199 A1 * | 1/2011 | Ross .................. | A61B 17/8875 606/1 |
| 2011/0313419 A1 | 12/2011 | Mullaney | |
| 2012/0004494 A1 | 1/2012 | Payne et al. | |
| 2012/0296234 A1 | 11/2012 | Wilhelm et al. | |
| 2013/0317367 A1 | 11/2013 | Shuler | |
| 2016/0113681 A1 * | 4/2016 | Singh ..................... | A61B 19/56 606/102 |
| 2017/0303967 A1 * | 10/2017 | Edelhauser ............ | A61B 17/62 |
| 2018/0055569 A1 * | 3/2018 | Wahl ..................... | A61B 34/10 |

FOREIGN PATENT DOCUMENTS

| | | |
|---|---|---|
| WO | 2009105479 A1 | 8/2009 |
| WO | 2010104567 A1 | 9/2010 |

OTHER PUBLICATIONS

International Search Report dated Oct. 12, 2012, in International Application No. PCT/US2012/043106.
S&N Fracture Reduction and Deformity Correction Software, Surgical Technique (2004).
S.V. Sreenivasan et al., "Closed-Form Direct Displacement Analysis of a 6-6 Stewart Platform," Mech. Mach. Theory, vol. 29, No. 6, pp. 855-864, 1994.
Smith and Nephew, Tailor Spatial Frame, 2005.

* cited by examiner

| Date | Day | Strut 1 (Red) | Strut 2 (Orange) | Strut 3 (Yellow) | Strut 4 (Green) | Strut 5 (Blue) | Strut 6 (Violet) | View |
|---|---|---|---|---|---|---|---|---|
| 01/01/01 | 0 | 150 | 145 | 140 | 135 | 160 | 160 | View |
| 01/02/01 | 1 | 151 | 144 | 146 | 138 | 159 | 156 | View |
| 01/03/01 | 2 | 151 | 142 | 151 | 141 | 158 | 152 | View |
| 01/04/01 | 3 | 152 | 141 | 157 | 144 | 158 | 148 | View |
| 01/05/01 | 4 | 153 | 139 | 162 | 147 | 157 | 144 | View |
| 01/06/01 | 5 | 153 | 138 | 168 | 150 | 156 | 140 | View |
| 01/07/01 | 6 | 154 | 137 | 173 | 154 | 155 | 137 | View |
| 01/08/01 | 7 | 155 | 135 | 179 | 157 | 154 | 133 | View |
| 01/09/01 | 8 | 156 | 134 | 184 | 160 | 154 | 129 | View |
| 01/10/01 | 9 | 156 | 132 | 190 | 163 | 153 | 125 | View |
| 01/11/01 | 10 | 157 | 131 | 195 | 166 | 152 | 121 | View |

METHODS AND SYSTEMS FOR ADJUSTING AN EXTERNAL FIXATION FRAME

CROSS-REFERENCE TO RELATED APPLICATIONS

The present application is a continuation of U.S. patent application Ser. No. 14/263,240, filed Apr. 28, 2014, which is a divisional of U.S. patent application Ser. No. 13/167,101, filed Jun. 23, 2011, the disclosures of which are both hereby incorporated by reference herein.

BACKGROUND OF THE INVENTION

The present disclosure relates to methods, tools and systems for adjusting an external fixation frame. More particularly, the present disclosure relates to methods tools and system for repositioning the components of an external fixation frame according to a correction plan.

The external fixation market can be divided into two major segments: acute trauma and reconstructive. The customers, products, and needs of each segment are distinctly different. The trauma segment is dominated by modular fixators. These frames are characterized by limited componentry and very rapid application. Consequently, they are known for being fairly simple products. Most of these frames are used for temporizing fixation and quite often are only on the patient for hours or days.

The reconstructive segment leans heavily toward ring fixation. Ring fixators, such as the well known Ilizarov frame, are very popular. Such frames are shown in U.S. Pat. Nos. 4,365,624; 4,615,338; 4,978,348; 5,702,389; and 5,971,984. Their use of a combination of pins and wires to achieve a variety of polyaxial pin/wire attachments provides stability. They can accomplish a full six degrees of freedom and, when applied and managed well, can correct primary deformities while not creating secondary deformities. Rotational deformities are the sole domain of the ring fixator. However, mastery of the techniques and the products themselves can be a long and daunting process that it is not attractive to many users.

It is often necessary to realign, reposition and/or securely hold two bone elements relative to one another. For example, in the practice of medicine, bone fragments and the like must sometimes be aligned or realigned and repositioned to restore boney continuity and skeletal function. At times, this may be accomplished by sudden maneuver, usually followed by skeletal stabilization with cast, plate and screws, intramedullary devices, or external skeletal fixators.

A bone fragment can be moved, in general, from its original position as in a nonunion or malunion or from its intended position as in congenital deformities along six separate movements or degrees of freedom, a combination of three orthogonal translational axes (e.g., typical "X," "Y" and "Z" axes) and three orthogonal rotational axes (e.g., rotation about such typical "X," "Y" and "Z" axes).

External fixation devices are attached to the boney skeleton with threaded and/or smooth pins and/or threaded and/or smooth and/or beaded wires. Such constructs are commonly referred to as orthopaedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

A circumferential external fixator system was disclosed by G. A. Ilizarov during the early 1950s. The Ilizarov system includes at least two rings or "halos" that encircle a patient's body member (e.g., a patient's leg), connecting rods extending between the two rings, transfixation pins that extend through the patient's boney structure, and connectors for connecting the transfixation pins to the rings. Use of the Ilizarov system to deal with angulation, translation and rotation is disclosed in "Basic Ilizarov Techniques," *Techniques in Orthopaedics®*, Vol. 5, No. 4, December 1990, pp. 55-59.

Prior art orthopaedic external fixators differ in their ability to move or adjust one bone fragment with respect to the other in a gradual fashion. Some allow gradual translation, others allow gradual rotation about two axes. The Ilizarov system can provide an external fixation device that could provide gradual correction along and about six axes; however, such a device would require many parts and would be relatively complicated to build and use in a clinical situation.

Often orthopaedic external fixators such as Ilizarov fixators must be repositioned after their initial application. Such modification may be necessary to convert from one correctional axis to another or to convert from an initial adjustment type of fixator to a weight bearing type of fixator, some of the correctional configurations not being stable enough for weight bearing.

A "Steward platform" is a fully parallel mechanism used in flight and automotive simulators, robotic end-effectors, and other applications requiring spatial mechanisms with high structural stiffness and includes a base platform, a top platform, and six variable limbs extending between the base and top platforms. See S. V. Sreenivasan et al., "Closed-Form Direct Displacement Analysis of a 6-6 Stewart Platform," *Mech. Mach. Theory*, Vol. 29, No. 6, pp. 855-864, 1994.

Taylor et al. U.S. Pat. No. 5,702,389, which entire disclosure is incorporated by reference herein, relates to a fixator that can be adjusted incrementally in six axes by changing strut lengths only, without requiring joints to be unclamped, etc. This patent includes a first ring member or swash plate for attachment relative to a first bone element; a second ring member or swash plate for attachment relative to a second bone element. Six adjustable length struts having first ends movably attached to the first member and second ends movably attached to the second member are provided. The first ends of the first and second struts are joined relative to one another so that movement of the first end of one of the first and second struts will cause a corresponding movement of the first end of the other strut, with the first ends of the third and fourth struts joined relative to one another so that movement of the first end of one of the third and fourth struts will cause a corresponding movement of the first end of the other strut. The third and fourth struts and fifth and sixth struts are similarly joined. Second ends of the first and sixth struts joined relative to one another so that movement of the second end of one of the first and sixth struts will cause a corresponding movement of the second end of the other strut. Second ends of the second and third struts and fourth and fifth struts are formed in a similar manner. Thus, changing the length of the struts effects reposition of the bone segments. The mathematics of this adjustment is set forth in the patent and may be programmed into a computer for use with the tool of the present invention.

As discussed above, most external fixators should be adjusted over a period of time to reposition bone segments. The adjustment of the external fixation may be implemented according to a "prescription" or correction plan. Physicians may adjust the external fixator at precise times over a period of time (e.g, on a daily basis for three weeks). Patients, however, may not desire to visit the physician's office every time an adjustment is needed. For this reason, many external fixators can be adjusted by the patients themselves without the assistance of a physician. The adjustment of the external fixator should nonetheless strictly comply with the predetermined correction plan. In some occasions, patients may not adjust their own external fixator according to the correction plan for a variety of reasons. For instance, patients may not understand how to use the external fixator correctly. In addition, when the patients themselves adjust the external fixators, physicians may not even know whether patients are in fact adjusting the external fixators according to the correction plan. For the foregoing reasons, it is desirable to provide a tool, system and/or method for helping a patient implement a correction plan in an external fixator.

BRIEF SUMMARY OF THE INVENTION

The present disclosure relates to methods, systems and tools for adjusting an external fixation frame according to a correction plan. In one embodiment, a system generally includes an identification mechanism, a tool and a processor. The identification mechanism is adapted to identify each of a plurality of adjustment elements or screws, for example, of an external fixation system. The tool is adapted to adjust the external fixation frame according to a predetermined correction plan by rotating the plurality of screws and includes a processor. The processor is configured to: receive correction plan data including the predetermined correction plan, the predetermined correction plan including a schedule of adjustment times and degree of rotation of each of the plurality of screws; receive identification data from the identification mechanism; and determine a degree of rotation of at least one of the plurality of the screws based on the correction plan data and the identification data.

The identification mechanism may include RFID tags attached to each of the plurality of screws. Each RFID tag includes identification data identifying each of the plurality of screws. The tool may further include an RFID reader adapted to read the identification data of the RFID tags.

The system may further include a bus device adapted to establish communication, whether hard wired or wireless, to allow data transfer between the processor of the tool and an external processor. The bus device may include an UBS device. The external processor may be coupled to a memory module adapted to store at least one of the correction plan data or the identification data. The system may also allow for data transfer from the tool back to the external processor.

The tool of the system described above may further include a memory module adapted for storing at least one of the correction plan data or the identification data. The tool may include a driver adapted to engage and rotate each of the plurality of screws and a motor connected to the driver and adapted to rotate the driver. In addition, the tool may include a controller electronically coupled to the motor and adapted to control the motor based on the correction plan data and the identification data. Moreover, the tool may include an angular position sensor coupled to the motor and adapted to determine an angular position of the driver. The angular position sensor may include a rotary encoder.

The tool described above may include an alarm connected to the process and adapted to be actuated at adjustment times and a clock for measuring time and allowing the processor to actuate the alarm at the adjustment times. The alarm may include a buzzer adapted to generate an audio signal at adjustment times.

In addition, the tool may include a display unit connected to the processor and adapted to display correction plan data and a power supply connected to the processor. The power supply may include a portable battery. The tool may further include an input device adapted to accept instructions from a user. The input device may include a keypad.

As discussed above, the present disclosure also relates to tools for implementing a correction plan in an external fixation frame having a plurality of screws. In one embodiment, the tool includes a driver adapted to engage and rotate each of a plurality of screws of an external fixation frame; a motor coupled the driver and adapted to rotate the driver; a controller connected to the motor and configured to control operation of the motor; and a processor. The processor is configured to: receive correction plan data; receive identification data including information for identifying at least one of the plurality of screws; determine movement of at least one of the plurality of the screws based on the correction plan data and the identification data; and send signals indicative of the determined movement to the controller in order to rotate at least one of the plurality of screws according to a predetermined correction plan.

The tool may further include an RFID reader adapted to receive signals containing identification data and originating from RFID tags attached to each of the plurality of screws. Moreover, the tool may include a bus device adapted to establish communication and allow data transfer between the processor of the tool and an external processor. The bus device may be a UBS device. In addition, the tool may include an angular position sensor coupled to at least one of the motor or the driver. The angular position sensor is adapted to measure an angular position of the driver. The angular position sensor may include a rotary encoder.

The correction plan data may include adjustment times for adjusting the external fixation frame. The tool may include an alarm connected to the process and adapted to be actuated at adjustment times.

The present disclosure further relates to a computer readable medium including instructions that, when executed by a processor, causes the processor to perform the certain steps. In one embodiment, the processor is adapted to perform the following steps: receiving correction plan data including information about a correction plan for adjusting an external fixation frame, the correction plan including a list of adjustment times and positions for each of a plurality of screws of the external fixation frame; receiving identification data including information for identifying at least one of the plurality of screws of the external fixation frame; and determining movement of at least one of the plurality of screws based on the correction plan data and the identification data.

The present disclosure also relates to methods for implementing a correction plan in an external fixation frame having a plurality of screws. In one embodiment, the methods includes the following steps: receiving correction plan data including information about a correction plan for adjusting an external fixation frame, the correction plan including a list of adjustment times and positions for each of a plurality of screws of the external fixation frame; receiving identification data including information for identifying at least one of the plurality of screws of the external fixation frame; determining movement of at least one of the plurality of screws based on the correction plan data and the identification data using a processor; and moving at least one of the plurality of screws according to the movement determined by the processor.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

FIG. 9 is an exemplary correction plan in a table form; and

DETAILED DESCRIPTION

Figure 1:
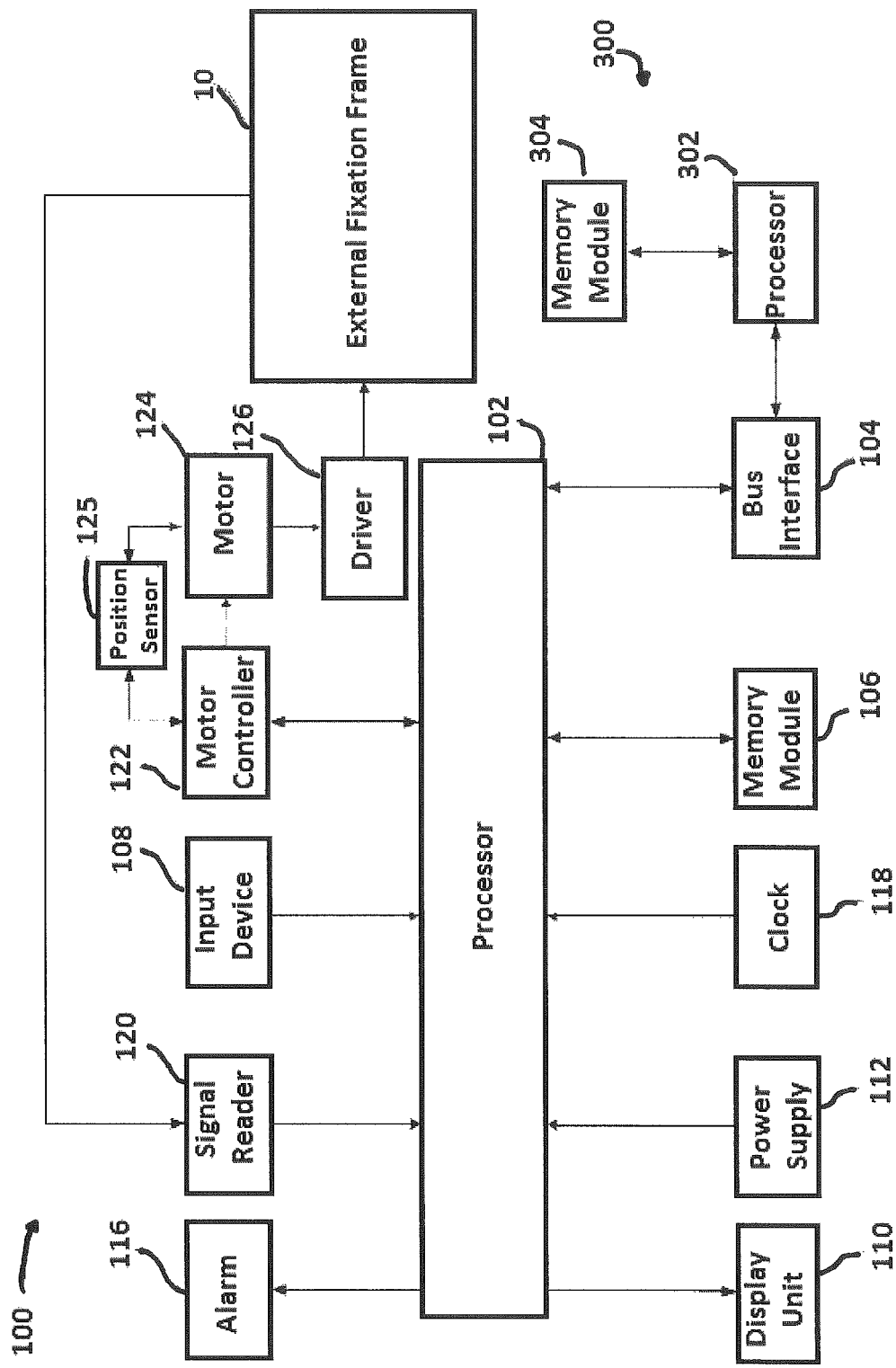
FIG. 1 is a schematic diagram of a system for adjusting an external fixation frame in accordance with an embodiment of the present disclosure.

The present disclosure will now describe in detail embodiments of methods and systems for adjusting an external fixation frame with reference to the drawings in which like reference numerals designate identical or substantially similar parts in each view. As used herein, "clinician" refers to a physician, surgeon, nurse or other care provider and may include support personnel.

FIG. 1 schematically depicts a tool or system 100 for adjusting any suitable external fixation frame 10. In general, the system or tool 100 includes processor 102, such as a microprocessor or central processing unit, capable of executing instructions for adjusting an external fixation frame 10. The processor 102 may include any suitable bus interface 104 for establishing communication between tool 100 and an external host computer 300, such as a personal computer. Suitable bus interfaces 104, include, but are not limited to Universal Serial Bus (UBS), a serial port, a parallel port, IEEE 1394 interface and Ethernet bus. Regardless of its specific type, bus interface 104 allows transfer of data between tool 100 and host computer 300. Host computer 300 includes a processor 302 for executing instructions and a memory module 304 for storing data. The bus interface 104 allows data stored on memory module 304 to be transferred to the tool 100. The data transfer between tool 100 and host computer 300 may be performed directly or indirectly. For example, data may be transferred between tool 100 and host computer 300 through a network, such as the Internet. The tool 100 may include a memory module 106 to store data, including data transferred from host computer 300. The processor 102 can therefore retrieve and process data from memory module 106. If host computer 300 is connected to tool 100 through bus interface 104, the processor 102 can also retrieve and process data stored on the memory module 304 of host computer 300.

With continued reference to FIG. 1, tool 100 may further include an input device 108 for inputting information. Input device 108 is adapted to accept instructions from a user and is connected to processor 102. In some embodiments, input device 108 may include a keypad having a plurality of alphanumeric keys and/or function keys configured to be actuated by users. Users may actuate these keys by, for example, depressing and releasing the keys. Input device 108 may additionally or alternatively include any other suitable device, means or mechanisms for entering information into tool 100, such a computer mouse, touchpad, trackball, and touch screen. In one embodiment, input device 108 includes a touchpad having a flat, touch sensitive screen, which tracks the movement of a finger or stylus across it.

The tool 100 may include a display unit 110 capable of displaying images. The display unit 110 is connected to processor 102 and may include liquid crystal display (LCD) panel. As discussed in detail below, display unit 100 may show information pertinent to the use of tool 100.

Any suitable power supply 112 may be coupled to processor 102 for energizing tool 100. Power supply 112 may include a DC or AC power source and/or a battery. The battery may be rechargeable.

The tool 100 may additionally include an alarm 116 capable of generating an audio signal or vibrations. The alarm 116 is connected to processor 102. As discussed in detail below, processor 102 can execute instructions to activate alarm 116. Alarm 116 may include a buzzer or any other device, means, or mechanism adapted for generating a sound or a vibration. As used herein, the term "sound" refers to one or more audio signals across the audible frequency range. Processor 102 may be connected to a clock 118 for measuring time. Clock 118 allows the processor 102 to actuate the alarm 116 at specified times.

The tool 100 may further include a signal reader 120, such as a radio-frequency identification (RFID) reader, capable of reading a signal from a radio-frequency transmitter on each drive element on the frame of, as described below. This signal is indicative of the identification of a specific screw or worm gear of the external fixation frame 10. For example, the screws may be identified by a number or letter. As discussed in detail below, each worm gear may have one or more identification tags, such as an RFID tag, configured to send a signal to be read by the signal reader 120. The signals stemming from the identification contain identification data for identifying each of the screws of the external fixation frame 10. For example, the identification data may be, for example, a number or letter associated with a specific screw.

The screws of external fixation frame 10 may be rotated by a driver 126 of tool 100. Driver 126 is adapted to engage and rotate the screws of external fixation frame 10. A motor 124 is connected to the driver 126. Upon activation, motor 124 can rotate driver 126. The operation and activation of motor 124 is controlled by a motor controller 122 connected to processor 102. The motor controller 122 is electronically connected to an angular position sensor 125. Angular position sensor 125 may include a synchro, a resolver, a rotary variable differential transformer (RVDT), a rotary potentiometer and/or any suitable rotary encoder. Suitable rotary encoders for angular position sensor 125 include, but are not limited to, a quadrature encoder and an absolute encoder. The angular position sensor 125 may be disposed on the shaft of motor 124, on the driver 126, or on the screws. Regardless of its location, the angular position sensor 125 can determine the angular position of the driver 126 and the screw attached to the driver. During operation, motor controller 122 controls the operation of driver 126 based on the instructions received from processor 102 and signals received from angular position sensor 125. The driver 126 in turns rotates a screw to adjust external fixation frame 10.

The tool 100 may be utilized in conjunction with any suitable external fixation frame. In an exemplary embodiment, tool 100 is used to adjust the external fixation frame 10 depicted in FIG. 2. In the interest of brevity, the present disclosure merely includes a brief description of external fixation frame 10. A suitable external fixation frame is described in detail in U.S. patent application Ser. No. 12/661,015 filed on Mar. 9, 2010, the entire disclosure of which is incorporated by reference herein. Another suitable external fixation frame is described in U.S. patent application Ser. No. 12/157,612 filed Jun. 11, 2008, the entire disclosure of which is incorporated herein by reference. The mathematics of the incremental adjustments is described in these applications.

Figure 2:
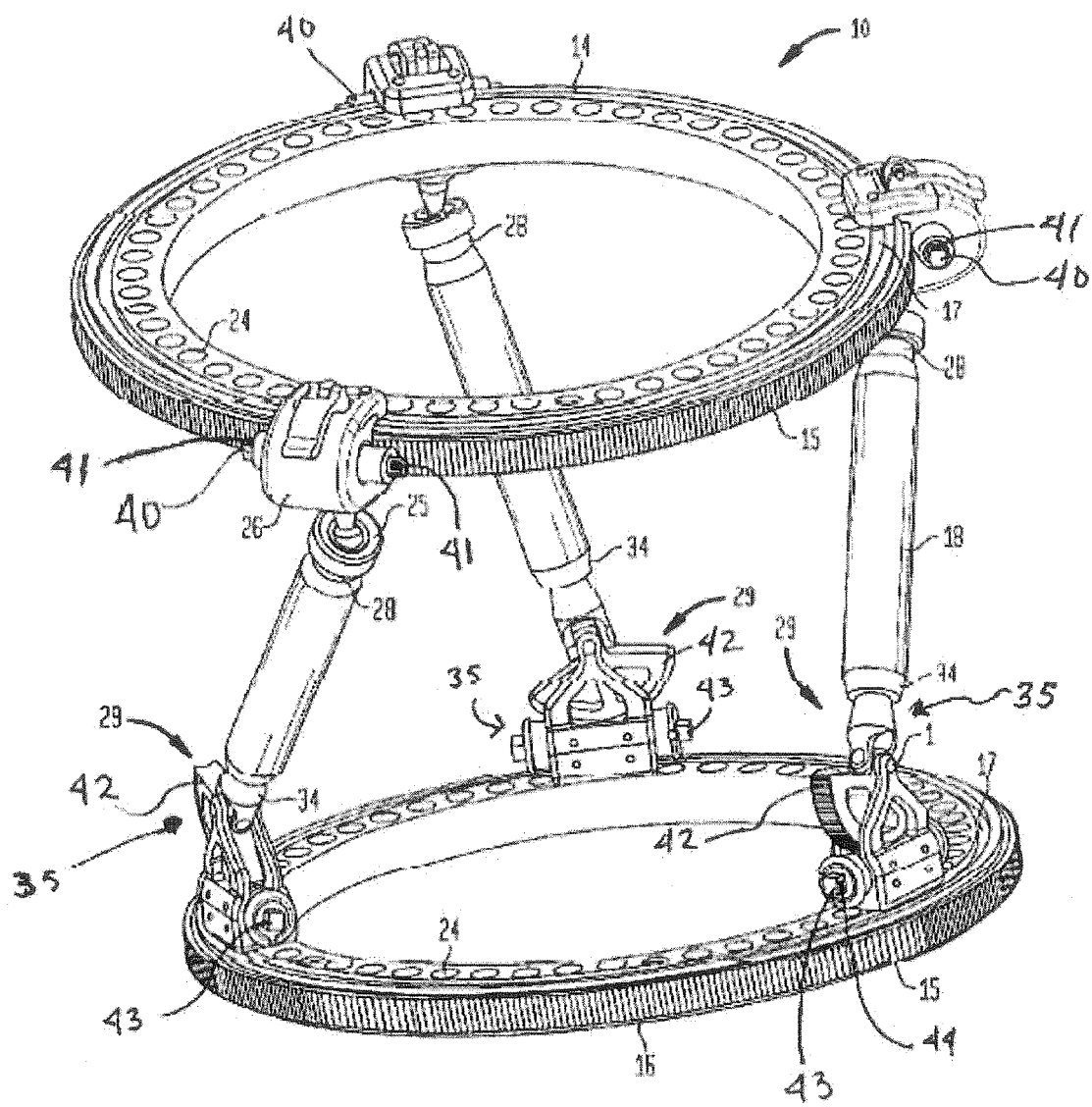
FIG. 2 is an isometric view of an external fixation frame that can be used in conjunction with the system schematically depicted in FIG. 1.

As seen in FIG. 2, external fixation frame 10 may be utilized with any long bone, in particular, the tibia and the femur, and includes a first ring 14 and a second ring 16. In operation, second ring 16 remains stationary, while ring 14 moves relative to the stationary ring 16. In some embodiments, both rings 14, 16 are identical. Each ring 14 includes a worm gear 15 formed around its outer circumference. Two grooves 17 are formed in the upper and lower surfaces of ring 14 around its circumference adjacent the worm gear 15. Ring 14 (or 16) may include a multi-level configuration with the upper and lower surfaces having alternate steps including through holes 24. In certain embodiments, rings 14, 16 are connected by three variable length struts 18. The three struts 18 have first ends 28 mounted to the first ring 14 via a connector 25 coupled to a sliding or shuttle unit 26, which is circumferentially moveable around ring 14. In several embodiments, the first ends 28 are connected to sliding or shuttle units 26 by a connector 25 having a ball or spherical joint. As is typical, the rings 14 and 16 are connected to a bone (e.g., tibia) by a plurality of bone pins or wires (not shown). In some embodiments, the pins or wires are connected to each ring 14, 16 by connection elements, which are located in one or more of a multiplicity of holes 24 around the circumference of the first and second rings 14 and 16. Although holes 24 are shown, any structure which locates the pins or wires with respect to the circumference of rings 14 and 16 can be utilized. Lower ends 34 of struts 18 are connected to lower ring 16 by standard universal-joints 35, which allow free rotation about only two axes rather than the three axes of the spherical joint at the first strut end 28.

Ring 14 may be coupled to a first bone element via pins or wires and, similarly, ring 16 is coupled to a second bone element by similar pins or wires. Shuttle units 26 are slidable about ring 14 in a track and are preferably driven by driver 126. Each shuttle unit 26 may include a worm or screw 40 configured to mesh with worm gear 15 of first ring 14. Each screw 40 can be driven by driver 126.

Identification tags 41, such as RFID tags, may be disposed on both sides of each screw 40. Each identification tag 41 stores identification data and is adapted to generate a signal indicative of the identification data of a particular screw 40. For instance, the identification data may include a number or letter assigned to a specific screw 40. Signal reader 120 is adapted to read the signals generated from each identification tag 41 to identify the screw 40 associated with a particular identification tag 41. In operation, rotation of screw 40 causes shuttle unit 26 to slide about ring 14, thus changing the position of strut 18. A second connector 29 between strut 18 and second lower ring 16 has a standard universal joint 35, which allows the strut to rotate freely about two axes, which may be oriented perpendicular to each other. Each universal joint 35 may include a gear portion 42 and screw 43. Screw 43 is adapted to engage gear portion 42 and may be rotated by driver 126.

Identification tags 44, such as RFID tags, may be disposed on both sides of each screw 43. Each identification tag 44 is adapted to send a signal containing identification data. The identification data includes information distinguishing a particular screw 43 from others screws of external fixation frame 10. Thus, each identification tag 44 is configured to generate a signal indicative of the location and identity of a particular screw 43 with respect to the entire external fixation frame 10. In addition, the signal generated by identification tag 44 may be indicative of the side of the screw 43 where the tag is located. Signal reader 120 is adapted to read the signal generated by each identification tag 44 in order to identify the screw 43. Although the drawings show screws 40a and 43, external fixation frame may alternatively include any drive element capable of being driven by a driver. Signal reader 120 and identification tags 41 and 44 collectively form an identification mechanism adapted to identify each and every screw 40 and 43 of external fixation frame 10. During operation, rotation of screw 43 causes gear portion 42 to pivot about a pin 1, thereby causing strut 18 to change its orientation relative to the rings 14 and 16. Thus, each of the three sliding shuttle units 26 may be independently controlled and the three connectors 29 at the second ring 16 may be independently controlled so that the ring 14, and therefore the bone element attached to ring 14, can be positioned in proper alignment with ring 16 and the bone element attached to ring 16. Rings 14 and 16 can be repositioned after their initial alignment as desired by the surgeon. In addition, the movement can be programmed into a processor, which can automatically increment movement, for example, on a daily basis. Each strut 18 may have a variable or fixed length.

Figure 3:
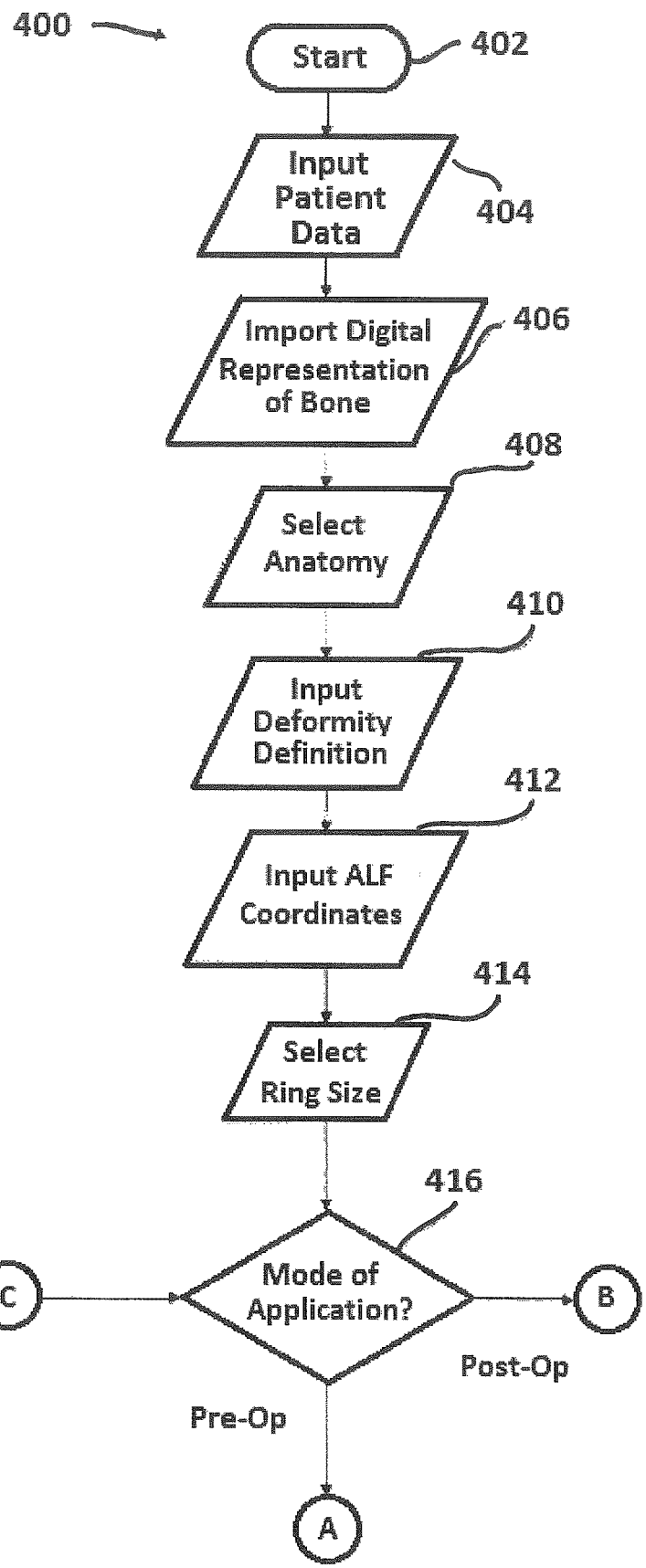
FIGS. 3-4 illustrate a flowchart showing the steps executed by an adjustment application.

With reference to FIGS. 1 and 3, the movement of external fixation frame 10 can be controlled by a computer or processor 102 of tool 100. As discussed above, the processor 102 of tool 100 can communicate and interact with host computer 300. Host computer 300 can store and execute an adjustment application to execute a process 400 for controlling the movement of external fixation frame 10 over a predetermined period of time. The memory module 304 of host computer 300 can store the data and/or instructions necessary to run the adjustment application using processor 302. The adjustment application may be a web-based application.

As illustrated in FIG. 3, the adjustment application starts at block 402. At block 404, adjustment application asks the clinician to input certain patient data. Patient data may include general information about the patient to be treated, such as name, age, weight, height, or any other information useful to identify an/or treat the patient. The adjustment application then asks the clinician to import one or more digital representations of the bone to be treated, at block 406. The clinician may import a digital representation of the bone into memory module 304. This digital representation of the bone may be in any suitable format. Suitable formats include, but are not limited to, Digital Imaging and Communications in Medicine (DICOM) data and digital x-rays images.

The adjustment applicant subsequently asks the clinician to select the anatomy to be corrected. In response, the clinician may select the bone to be corrected by the external fixation frame 10, at block 408. Once an anatomy has been selected, the adjustment application prompts the clinician to input a deformity definition for the selected anatomy at block 410. As used herein, "deformity definition" refers to the anatomical misalignment that the external fixation frame 10 will correct. The deformity definition (also referred as deformity data) may include information about the rotation, translation, angulation, length and vertical translation of the selected bone or anatomy.

The adjustment application then asks the clinician to input anatomical limiting factors (ALF) coordinates at block 412. ALF refers to factors that may limit the movement of the external fixation frame 10. For example, the correction of the selected bone should be conducted at gradual rate of bone distraction. A rapid rate of distraction may result in a fibrous union in which the bone pieces are joined by fibrous, rather than osseous tissue. Conversely, an atypically slow distraction rate may result in early bone consolidation. It is therefore desirable to control the rate of bone distraction by inputting specific coordinates for the movement of external fixation frame 10. The rate of bone distraction may be, for example, set at 1 millimeter per day. Another ALF may be the position of the patient's nerves. During correction of the injured or misaligned bone, stretching of the nerves may occur. Stretching of the nerves must not be too rapid to avoid nerve injury. Another ALF can be the patient's skin. If the skin has been compromised, for example in case of an open fracture that part of the skin should not be stretch too rapidly to allow the skin to heal.

At block 414, the adjustment application allows the clinician to select the appropriate ring size in accordance with the patient's anatomy. After selecting the ring size, the adjustment application asks the clinician whether the application should be executed in pre-operation (Pre-Op) or post-operation (Post-Op) mode, at block 416. The Pre-Op mode is an optional planning tool designed to virtually test the movement of the external fixation frame 10 without attaching the external fixation frame to a bone. In the Post-Op mode, the adjustment application runs while the external fixation frame 10 is attached to a bone to correct that bone.

If the clinician selects the Pre-Op mode of the adjustment application, the application determines all possible strut combinations based on, among other things, the positions of the rings 14 and 16, at block 418, as discussed in detail below. The adjustment application then allows the clinician to select a strut combination at block 420 out of all the possible strut combinations. Once the clinician has selected a strut combination, the adjustment application generates a correction plan at block 422, as discussed in detail below. The host computer 300 then displays the correction plan and a simulation thereof via any suitable output device, such as a monitor or screen, at block 424. The host computer 300 also displays a report for the specific patient at block 426. The report may include, but is not limited to, patient data, selected anatomy, correction plan data, inputted deformity definition, inputted ALF coordinates, etc. The report may be displayed through an output device, such as a monitor, which is connected to host computer 300. After running the adjustment application in the optional Pre-Op mode, the clinician may run the adjustment application in the Post-Op mode to correct the patient's bone. Accordingly, the adjustment application allows the clinician to select again the mode of application at block 416.

If the clinician selects the Post-Op mode at block 416, the adjustment application determines the position of the movable ring 14 at block 428. As discussed above, rings 14 is adapted to move during operation, while ring 16 remains stationary. The adjustment application may determine the position of the movable ring based on, among other things, the inputted digital representations of the bone, anatomy, deformity definition, ALF coordinates and the strut lengths. Subsequently, the adjustment application generates a correction plan at block 430, as discussed in detail below.

After generating the correction plan, the host computer 300 displays the correction plan and a simulation thereof, at block 432, via an output device, such as a monitor or screen. In addition, the host computer 300 displays a report for the specific patient at block 434. The report may include, but is not limited to, patient data, selected anatomy, correction plan data, inputted deformity definition, inputted ALF coordinates, etc. The report may be displayed through an output device, such as a monitor, which is connected to host computer 300. The correction plan as well as all the necessary data is uploaded into tool 100 at block 436. The host computer 300 can be connected directly to tool 100 via bus interface 104. For example, a UBS cable may interconnect bus interface 104 and host computer 300. Alternatively, communication between host computer 300 and tool 100 may be established through a closed network or an open network, such and the Internet. If communication is established through a network, the tool 100 may be connected to the network through another computer. In such case, the tool 100 is connected to that computer via bus interface 104. That computer is in turn connected to the network and interacts and communicates with host computer 300. The adjustment application terminates, at block 438, after the correction plans is uploaded to tool 100.

Figure 4:
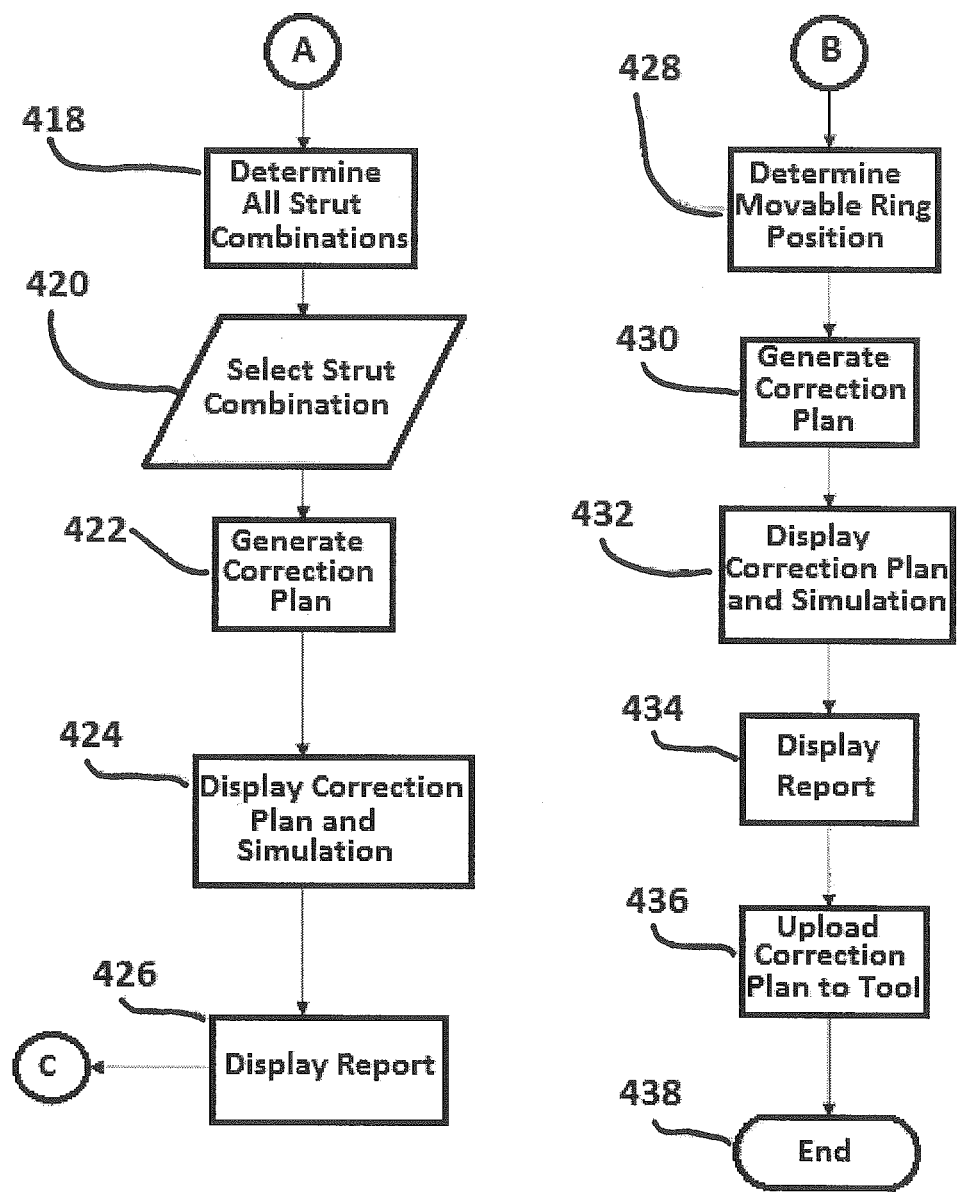
Figure 5:
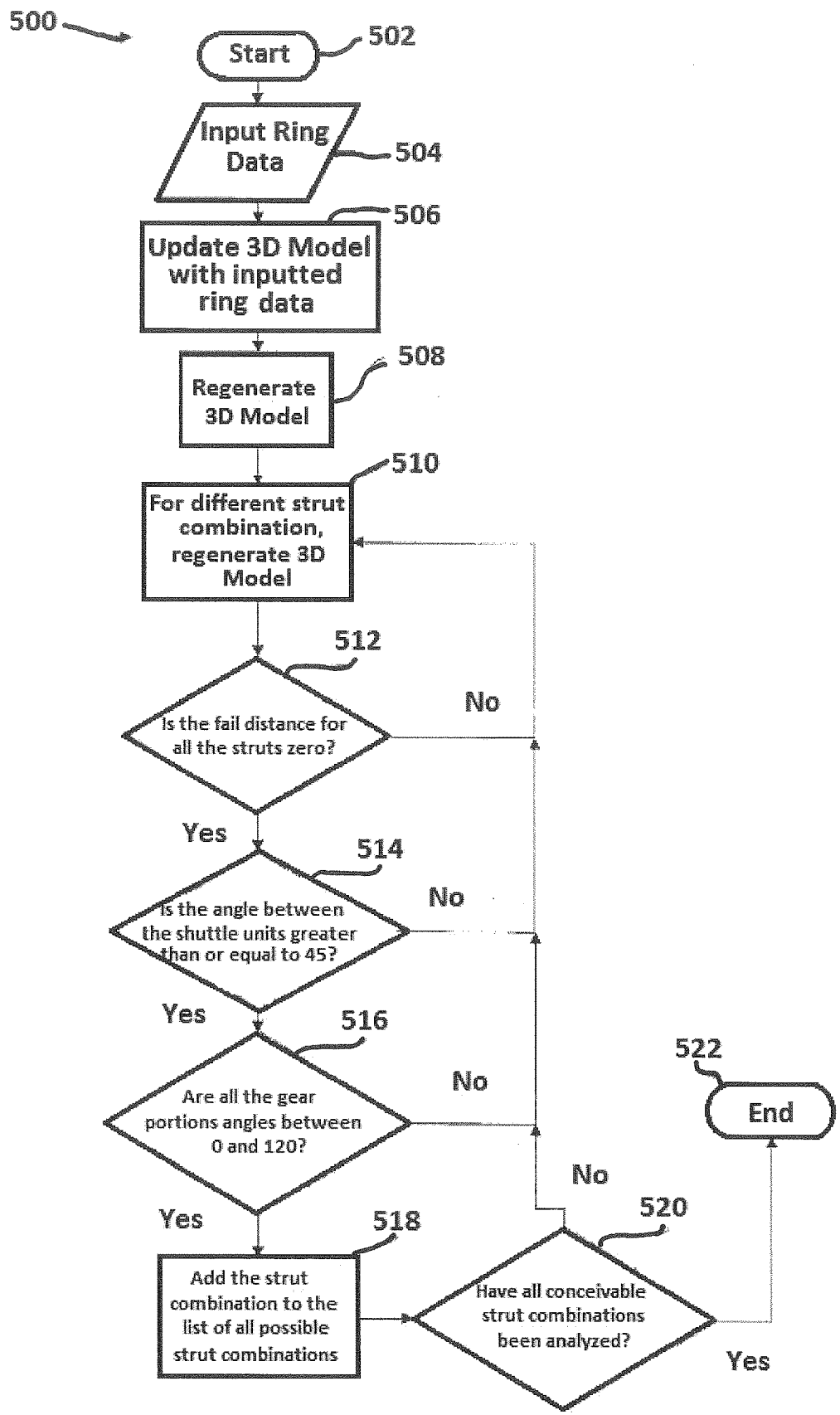
FIG. 5 is a flowchart illustrating a process for determining all possible strut combinations.

FIG. 5 illustrates a process 500 for determining all possible strut combinations in the Pre-Op mode of the adjustment application, as discussed above with respect to block 418 of FIG. 4. This process begins at block 502 of FIG. 5. To determine the possible strut combinations, the adjustment application allows the clinician to input ring data at block 504. Ring data may include, but is not limited to, sizes of both rings 14 and 16, three-dimensional position (i.e., X, Y, Z coordinates) of the ring 16 with respect to reference coordinates (i.e., origin) and the three-dimensional position (i.e., X, Y, Z coordinates) of ring 14 with respect to reference coordinates (i.e., origin). After inputting the ring data, the adjustment application updates a preloaded digital representation of external fixation frame 10 with the inputted ring data at block 504. The digital representation of external fixation frame 10 may be updated with the new dimensions, positions, offsets and angles of the rings 14 and 16. In one exemplary method, the digital representation of external fixation frame 10 (e.g., 3D digital model) may be created with any suitable 3D modeling or computer aided design (CAD) software, such as the Pro/E® or Creo Elements/Pro™ sold by Parametric Technology Corporation. The digital representation of external fixation frame 10 may be updated using any programming interface to the 3D modeling or CAD software. For instance, the digital representation of external fixation frame 10 may be updated with an application programming interface (API), such as the Java-based API J/Link™ sold by Parametric Technology Corporation. J/Link™, for example, integrates Pro/E® and Java, allowing the Pro/E® model to be modified with a Java program.

After the digital representation of data has been updated with the inputted ring data, the 3D modeling or CAD software regenerates the 3D model of the external fixation frame 10 and the patient's anatomy, at block 508, based on the initial strut combination. As used herein, a "strut combination" refers the struts 18 connected rings 14 and 16, which may have different sizes and/or length. For example, one strut combination may include struts 18 having the same lengths. Another strut combination may entail two struts 18 having the same lengths and a third strut having a different length. Yet another strut combination may include three struts 18 all having different lengths. Since external fixation frame 10 has a plurality of struts 18, it can have multiple strut combinations. At block 508, the CAD software regenerates a 3D model of external fixation frame 10 and the patient's anatomy with an initial strut combination.

At block 510, the 3D model is regenerated for a different strut combination. As discussed above, the 3D model may be regenerated using any suitable 3D modeling or CAD software. Once the 3D model of external fixation frame 10 and the patient's anatomy has been regenerated for the specific strut combination, the adjustment application determines, at decision block 512, whether the fail distance for any of the struts 18 is zero. Fail distance may be defined as a position of a strut outside of its possible position or angle with respect to a ring of fixation frame 10. If the fail distance for any of the struts 18 is not zero for the specific strut combination, then the adjustment application discards that strut combination and regenerates a 3D model for another strut combination at block 510. Conversely, if the fail distance for all the struts 18 is zero for the specific strut combination, then the adjustment application determines whether the angles between shuttle units 26 are each greater than or equal to 45° at decision block 514. If each of these angles is not greater than or equal to 45°, the adjustment application discards that strut combination and regenerates a 3D model for another strut combination at block 512. On the other hand, if each of these angles is greater than or equal to 45°, the adjustment application then determines whether each of the angles defined between each gear portions 42 and stationary ring 16, for that specific strut combination, is within a specified range, preferably between 0° and 120° at decision block 516. If any of these angles is not between 0° and 120°, the adjustment application then discards that specific strut combination and regenerates the 3D model for another strut combination. If each of these angles is between 0° and 120°, the adjustment application then adds the strut combination to a list of all possible combinations.

Once the specific strut combination has been added to the list of possible strut, the adjustment application determines whether all conceivable strut combinations have been analyzed by process 500 at decision block 520. If all conceivable strut combinations have been analyzed, the adjustment application terminates at block 522. On the other hand, if not all conceivable strut combinations have been analyzed, then the adjustment application regenerates a 3D model of external fixation frame 10 with a different strut combination at block 510 and analyzes such strut combination as described above.

As discussed above with regard to FIGS. 3 and 4, the adjustment application executes a process 400, which includes determining the position of a movable ring 14, at block 428, in the Post-Op mode. To determine the position of the movable ring 14, the adjustment application may execute the process 600 illustrated in FIG. 5.

Figure 6:
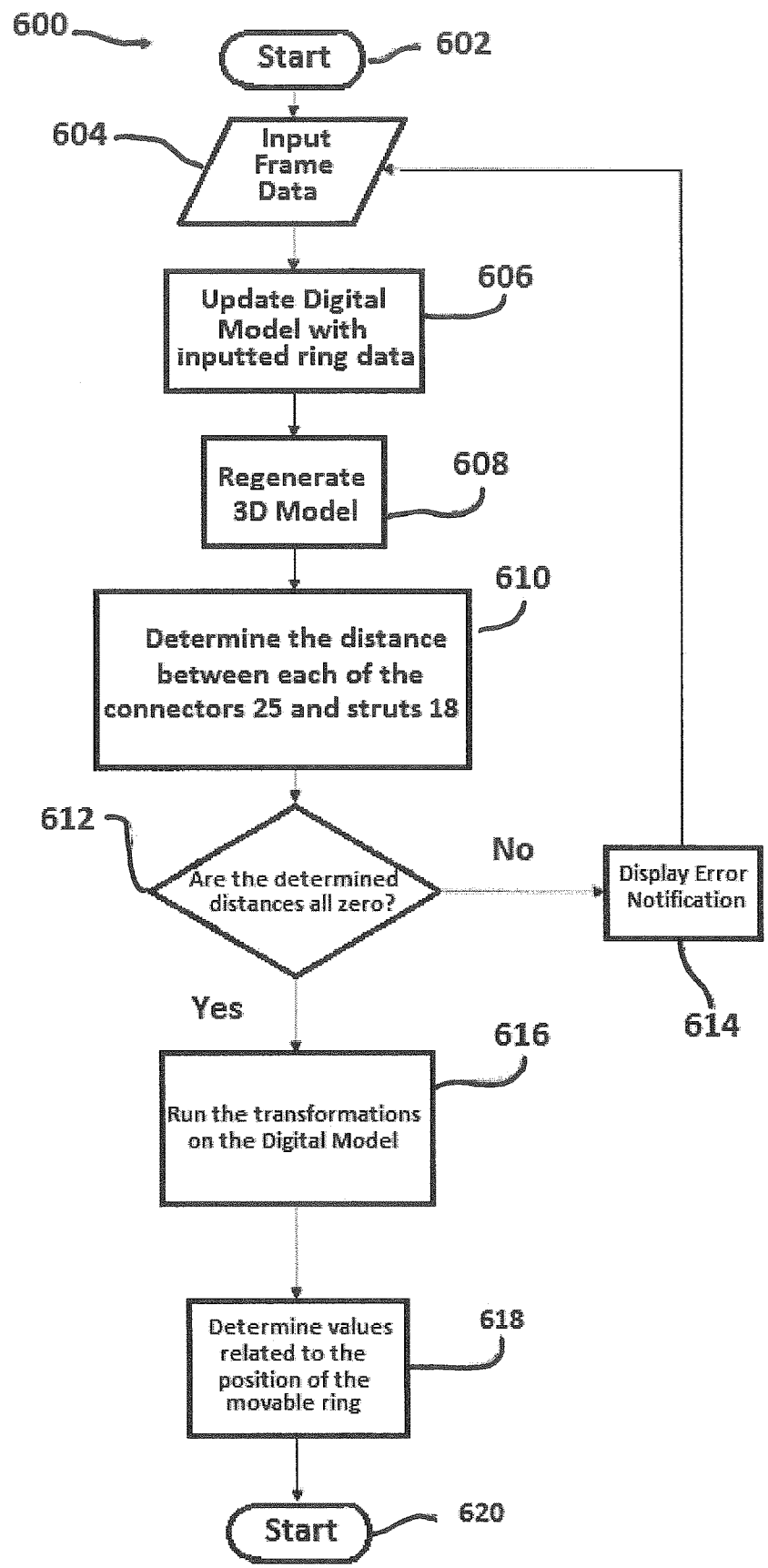
FIG. 6 is a flowchart illustrating a process for determining the position of the movable ring of the external fixation frame.

FIG. 6 illustrates the process 600 for determining the position of movable ring 14, which starts at block 602. The adjustment application allows the clinician to input frame data at block 604. Frame data may include, but is not limited to, sizes of both rings 14 and 16, the lengths of struts 18, orientation of shuttle units 26 and gear portions 42. The inputted information about the orientation of the shuttle units 26 and gear portions 42 may include the angles that each of the shuttle units 26 and gear portions 42 are with respect to the struts 18. After inputting the frame data, the adjustment application updates a preloaded digital representation of external fixation frame 10 (i.e., digital model) with the inputted frame data at block 606. The digital representation of external fixation frame 10 may be updated with the new dimensions, positions, offsets and angles of the rings 14 and 16. In one exemplary method, the digital representation of external fixation frame 10 (e.g., 3D model) may be created with any suitable 3D modeling or computer aided design (CAD) software, such as the Pro/E® or Creo Elements/Pro™ sold by Parametric Technology Corporation. The digital representation of external fixation frame 10 may be updated using any programming interface to the 3D modeling or CAD software. For instance, the digital representation of external fixation frame 10 may be updated with an application programming interface (API), such as the Java-based API J/Link™ sold by Parametric Technology Corporation. J/Link™, for example, integrates Pro/E® and Java, allowing the Pro/E® model to be modified with a Java program. After the digital representation of data has been updated with the inputted ring data, the 3D modeling or CAD software regenerates the 3D model of the external fixation frame 10 and the patient's anatomy, at block 608, based on the inputted frame data.

At block 610, the adjustment application determines distances between each of connectors 25 and the struts 14. At decision block 612, the adjustment application subsequently determines if all of the distances determined at block 610 are zero. If any of the determined distances is not zero, an error notification is displayed on any suitable output device, such as a monitor or screen, at block 614. The error notification may include the following message: "Invalid Input Parameters." After displaying the error notification, the adjustment application allows the clinician to new input frame data at block 604. If all the distances determined at block 610 are zero, the adjustment application runs the transformations on the digital model of external fixation frame 10, at block 616. As discussed above, the digital model may be created with any suitable 3D modeling or CAD software, such as the Pro/E® or Creo Elements/Pro™ sold by Parametric Technology Corporation. Then, the adjustment application determines values concerning the position of movable ring 14. These values may include the offset and orientation of the center of movable ring 14 in the coronal, sagital and axial planes. After determining these values, the process 600 ends at block 620.

As discussed above, the adjustment application can generate a correction plan either in the Pre-Op mode or Post-Op mode. To generate the correction plan, the adjustment application executes the process 700 depicted in FIG. 7. The process 700 begins at block 702 and then allows a clinician to input frame data at block 704. The frame data may include, but is not limited to the sizes of the rings 14 and 16, the osteotomy position, the three dimensional position and orientation of ring 14 with respect to an origin, deformity definitions in the coronal, sagital and axial planes, angles of the shuttle units 26 and gear portions 42 with respect the struts 18, and correction time. The correction time may be expressed in days.

Figure 7:
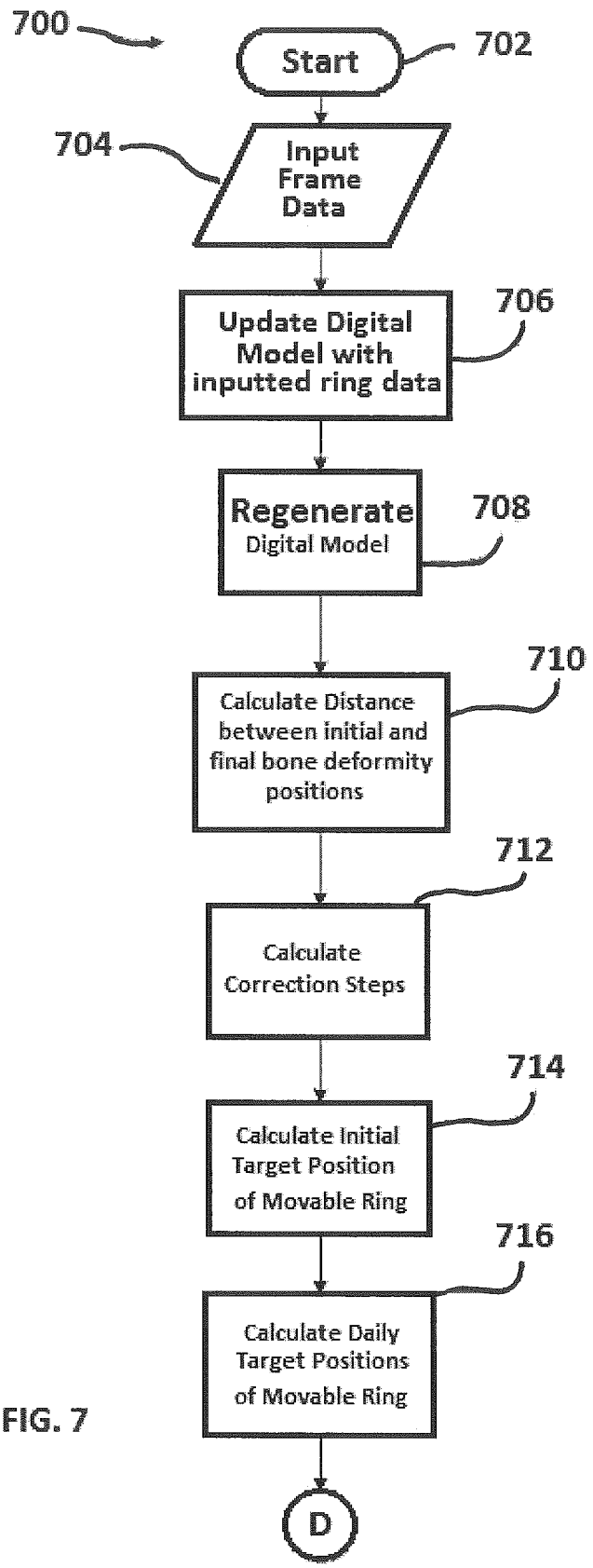
FIGS. 7 and 8 depict a flowchart illustrating a process for generating a correction plan.
Figure 8:
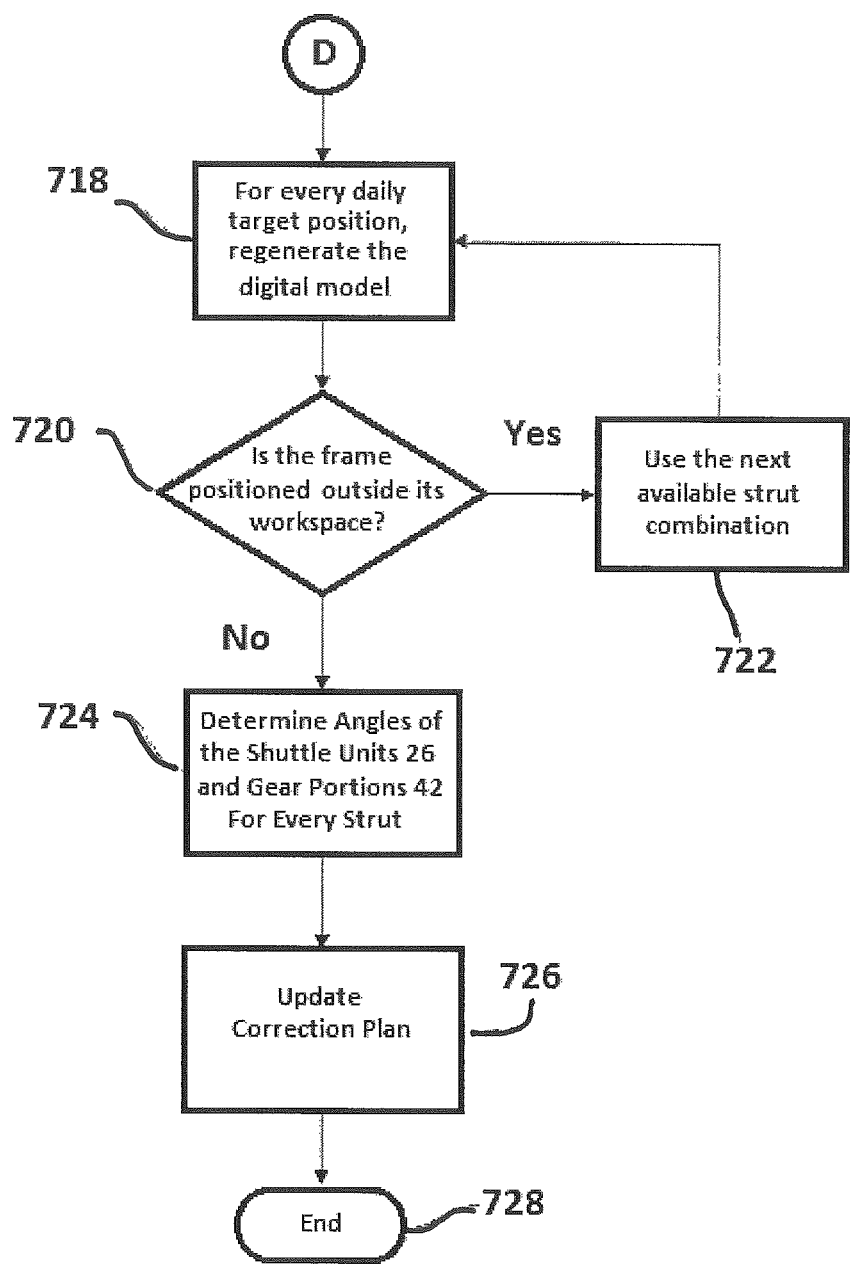

With continued reference to FIG. 7, after inputting the frame data, the adjustment application updates a preloaded digital representation of external fixation frame 10 (i.e., digital model) with the inputted frame data at block 704. The digital representation of external fixation frame 10 may be updated with the new dimensions, positions, offsets and angles of the rings 14 and 16. In one exemplary method, the digital representation of external fixation frame 10 (e.g., 3D digital model) may be created with any suitable 3D modeling or computer aided design (CAD) software, such as the Pro/E® or Creo Elements/Pro™ sold by Parametric Technology Corporation. The digital representation of external fixation frame 10 may be updated using any programming interface to the 3D modeling or CAD software. For instance, the digital representation of external fixation frame 10 may be updated with an application programming interface (API), such as the Java-based API J/Link™ sold by Parametric Technology Corporation. J/Link™, for example, integrates Pro/E® and Java, allowing the Pro/E® model to be modified with a Java program. After the digital representation of data has been updated with the inputted frame data, the 3D modeling or CAD software regenerates the digital model of the external fixation frame 10 and the patient's anatomy, at block 708, based on the inputted frame data.

Once the digital model has been regenerated in the 3D modeling or CAD software, the adjustment application calculates the distance (d) between the initial bone deformity position and the final bone deformity position (i.e., reference point.) The adjustment application then calculates the correction steps. In one exemplary method, the correction time may be determined by dividing the distance (d) between the initial and final bone deformity positions by the inputted correction time. As discussed above, the correction time may be expressed in days.

The adjustment application subsequently calculates the initial target position of movable ring 14, at block 714, based on the initial position of movable ring 14 and the inputted deformity definitions. Then, the adjustment application calculates the daily target positions of movable ring 14, at block 716, based on the initial and final target positions of the movable ring 14 and the number of correction steps. At block 718, the adjustment application then regenerates the digital model of external fixation frame 10 for every daily target position using the movable ring position, the reference ring position, and the struts lengths. The digital model of external fixation frame 10 may be regenerated with any 3D modeling or CAD software, as described above.

After regenerating the digital model of external fixation frame 10, the adjustment application determines whether virtual model of the external fixation frame 10 is located outside of its workspace at any of the daily target positions at decision block 720. The external fixation frame 10 cannot move outside of its workspace. Accordingly, the correction plan should include daily target positions compatible with the workspace of the external fixation frame 10. If the digital model of external fixation frame 10 is outside the allowed workspace for any daily target position, the adjustment application employs the next available strut combination from the list of all possible strut combinations determined by the process 500 at block 722 and, subsequently, regenerates the digital model again for every daily target position at block 718. If the digital model of external fixation frame 10 is within its allowed workspace for every daily target position, the adjustment application then determines the angles of the shuttle unit 26 and gear portions 42 relative to the struts 18 at block 724. After determining these angles, the adjustment application updates the correction plan at block 726 with the angles determined at block 724. The updated correction plan may reflect changes in the strut combination. The updated correction plan or "prescription" may be in the form of a table, as shown in FIG. 9 and may include screw identification data (e.g., screw number or letter), amount of rotation (e.g., degrees or radians), direction of rotation (e.g., clockwise or counterclockwise), and frequency of rotation (e.g., in hours and minutes.) The process 700 ends after the adjustment application has updated the correction plan at block 728.

With reference to FIG. 1, tool 100 includes a processor 102 adapted to execute a correction application stored on memory module 106. Memory module 106 may store a correction plan data used by the correction application. The correction application may be used in conjunction with tool 100 to implement a correction plan algorithm or process.

Figure 10:
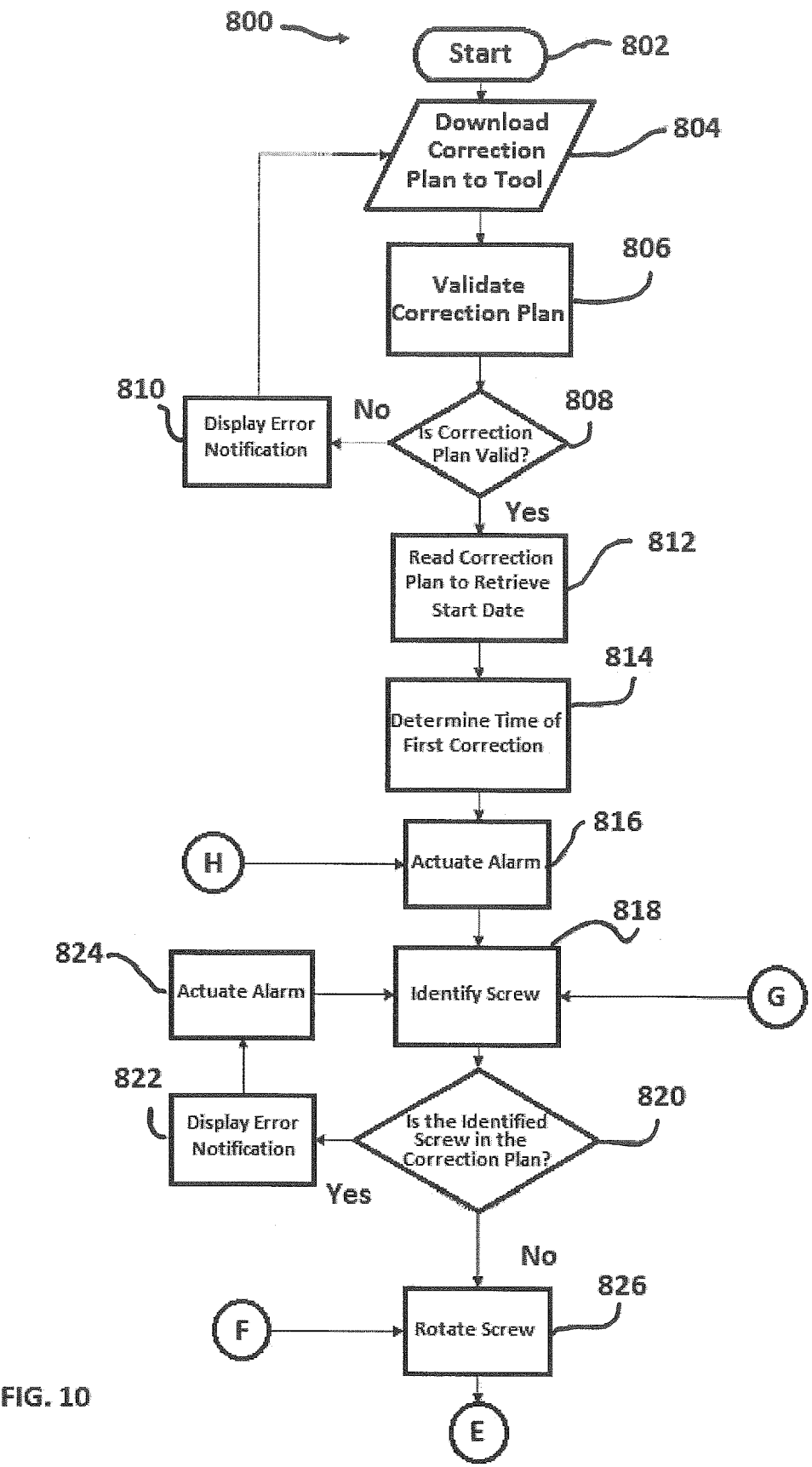
FIGS. 10-11 depict a flowchart illustrating a process for adjusting an external fixation frame according to a correction plan.
Figure 11:
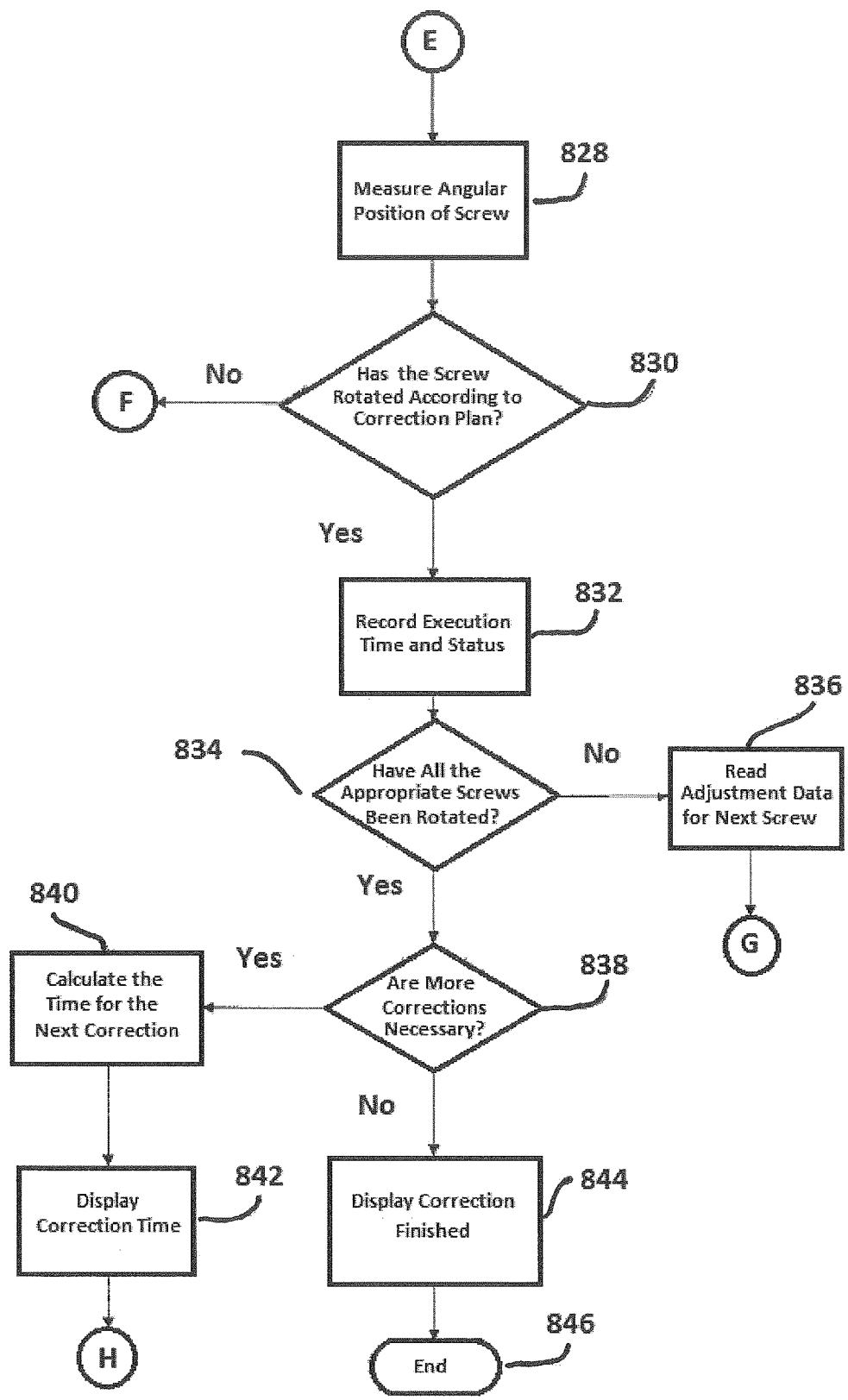

FIGS. 10 and 11 illustrate a flowchart of the correction algorithm or process 800, which starts at block 802. At block 804, correction plan data generated by adjustment application, as described above, is downloaded to tool 100. The correction plan data is stored on memory module 106 and may include, but is not limited to, screw identification information (e.g., screw number or letter), amount of rotation (e.g., degrees or radians), direction of rotation (e.g., clockwise or counterclockwise), and frequency of rotation (e.g., in hours and minutes.) The correction application then validates the correction plan data by, for example, verifying that the data is not corrupted. The clinician is also given the opportunity to validate the correction plan at decision block 808. Accordingly, the correction plan allows the clinician to input whether the correction plan is valid via input device 108 of tool 100. If the correction application or the clinician determines that the correction plan is not valid, the correction application displays an error notification or message, such as "Correction Plan Invalid," at block 810, and then allows the clinician or the patient to input a valid correction plan at block 804. The error notification may be displayed via display unit 110 of tool 100. If the correction plan is valid, the application plan reads the correction plan data stored on memory module 106 to retrieve the start date of the correction plan at block 812.

Based on the retrieved start date, the correction application determines or calculates the precise time (i.e., adjustment time) of the first correction, at block 814. The correction application then actuates alarm 116 to alert the patient that is time to execute a scheduled correction at block 816. Specifically, processor 102 receives a signal from clock 118 at the adjustment time. In response to this signal, the processor 102 sends a signal to alarm 115 to actuate it. At block 818, the patient or clinician may then activate the signal reader 120 of tool 100 to identify the screw to be rotated according to the downloaded correction plan. As discussed above, the signal reader 120 may be an RFID reader. The signal reader 120 is then moved close to a screw 40 or 43 to read signal generated by the identification tags 41 or 44 in each screw 40 or 43. Once the signal reader 120 reads the signal from the identification tags 41 or 44, the processor 102 of tool 100 identifies the screw. The correction application then determines whether the identified screw corresponds to the screw that needs to be rotated according to the downloaded correction plan at decision block 820. If the identified screw does not need to be rotated at that precise moment (i.e., scheduled adjustment time), an error notification is displayed via display unit 110, at block 822, and the alarm 116 is actuated at block 824 to indicate the user that the identified screw does not need to be rotated at the moment. The error notification may include an error message, such as "Invalid Screw." The error message may be displayed at the same time as the alarm is actuated. In response to the error notification, the user may use signal reader 120 to identify the appropriate screw 40 or 43.

If the signal reader 120 identifies the screw 40 that should be rotated according to the correction plan, the user may then securely engage driver 126 to the identified screw 40 or 43. Subsequently, the user activates the motor 124 to rotate the identified screw 40 or 43 at block 826. While the identified screw 40 or 43 rotates, the angular position sensor 125 measures the angular position of the rotating screw at block 828. The angular position sensor 125 sends 125 a signal indicative of the angular position of the identified screw 40 or 43 to the motor controller 122. Based on this signal, the motor controller 122 determines whether the identified screw 40 or 43 has been rotated according to the correction plan at block 830. If the screw has not been completely rotated in accordance with the correction plan, then the motor controller 124 instructs the motor 124 to continue rotating the driver 126 until the identified screw 40 or 43 has been rotated in accordance with the correction plan. Conversely, if the identified screw has been completely rotated according to the correction plan, the motor controller 122 instructs the motor 126 to stop rotating driver 126. The correction application then records when the identified screw was rotated (i.e., execution time) and the status of the rotated screw (e.g., angular position of rotated screw). This information may be stored on memory module 106.

The system preferably includes a safety feature to ensure that the adjustment elements are rotated the correct amount when being adjusted by the tool. In rare circumstances, the driver may disengage from the screw head during rotation. In such a case, the system would receive a signal response alerting it that the driver has disengaged from the screw head, allowing the tool to re-engage the adjustment element and to adjust the element the amount it would have been adjusted but for the previous disengagement.

At block 834, the correction application determines whether any other screw needs to be rotated immediately in accordance with the correction plan. If more screws need to be rotated, the processor 102 retrieves and reads the adjustment data for the next screw at block 836. Then, the user may identify the correct screw, at block 818, and rotate said screw as described above. On the other hand, if the correction plan does not provide for immediate rotation of other screws, the correction application determines whether any other corrections are necessary in the future, at decision block 838. If more corrections are necessary, the processor 102 determines or calculates the time for the next correction at block 840. At block 842, the correction time may be displayed through display unit 110. The clock 118 measures time and sends a signal to processor 102 at the next correction time. In response to this signal, the processor 102 actuates alarm 116 at block 816. The correction plan then executes the necessary steps to rotate the appropriate screws in accordance with the correction plan, as discussed in detail above. If no more corrections are necessary, the display unit 110 displays a message or notification indicating that the correction of bone has finished. The message may be, for example, "Correction Finished." The correction application then terminates process 800 at block 846.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of generating correction plans for treating a deformity in a bone of a patient with an external fixation frame comprising the steps of:
   importing into a computer application at least one digital representation of the deformed bone;
   selecting in the computer application an anatomy to be corrected by the external fixation frame, the anatomy corresponding to the deformed bone;
   inputting data into the computer application to define the deformity in the bone;
   after defining the deformity in the bone, operating the computer application in a pre-operative mode prior to attaching an external fixation frame to the patient comprising the steps of:
      inputting into the computer application desired positions of first and second rings of the external fixation system relative to the deformed bone;
      inputting into the computer application desired positions of a plurality of struts for coupling the first ring to the second ring by selecting one combination of possible strut combinations from a group of possible strut combinations, the group of possible strut combinations having been determined by the computer application based on the desired positions of the first and second rings; and
      based on the desired positions of the first and second rings and the desired positions of the plurality of struts, generating a first correction plan including target positions of the external fixation frame over time;
   coupling the first ring and the second ring to the deformed bone;
   coupling the first ring to the second ring with the plurality of struts; and
   operating the computer application in a post-operative mode after attaching the external fixation frame to the patient comprising the steps of:
      generating in the computer application a model of the external fixation frame, the model including a model first ring having a model position and orientation corresponding to an actual position and orientation of the first ring, a model second ring having a model position and orientation corresponding to an actual position and orientation of the second ring, and a plurality of model struts having model lengths corresponding to actual lengths of the plurality of struts, the model position and orientation of the model second ring having been determined by the computer application based on the model position and orientation of the model first ring and the model lengths of the plurality of model struts; and
      based on the model position and orientation of the model first ring, the model position and orientation of the model second ring, and the model lengths of the plurality of model struts, generating a second correction plan including target positions of the external fixation frame over time.

2. The method of claim 1, further comprising the step of inputting into the computer application coordinates of an anatomical limiting factor.

3. The method of claim 2, further comprising determining a rate of bone distraction based at least in part on the anatomical limiting factor.

4. The method of claim 1, wherein defining the deformity of the bone includes inputting into the computer application information selected from the group consisting of rotation, translation, angulation, length, and vertical translation of the bone.

5. The method of claim 1, further comprising displaying the first correction plan on a display device.

6. The method of claim 5, further comprising displaying a simulation of the first correction plan on the display device.

7. The method of claim 1, further comprising uploading the second correction plan to a tool for adjusting the external fixation frame.

8. The method of claim 7, wherein the tool is configured to adjust lengths of the plurality of struts.

9. The method of claim 8, wherein the tool includes a screwdriver portion.

10. The method of claim 1, wherein the group of possible strut combinations includes all possible strut combinations.

11. The method of claim 1, wherein, during the computer application determining the group of possible strut combinations, a potential strut combination is analyzed to determine whether any ones of a potential strut of the potential strut combination has a position or an angle with respect to the first ring or the second ring that is outside a possible position or a possible angle with respect to the first ring or the second ring.

12. The method of claim 11, wherein the potential strut combination is rejected if the computer application determines that any one of the potential struts of the potential strut combination has a position or an angle with respect to the first ring or the second ring that is outside the possible position or the possible angle with respect to the first ring or the second ring.

13. The method of claim 11, wherein the potential strut combination is added to the group of possible strut combinations if the computer application determines that each of the potential struts of the potential strut combination does not have a position or an angle with respect to the first ring or the second ring that is outside the possible position or the possible angle with respect to the first ring or the second ring.

* * * * *